US011203562B2

(12) United States Patent
Pappo et al.

(10) Patent No.: US 11,203,562 B2
(45) Date of Patent: Dec. 21, 2021

(54) SEPARATION OF PHENOL ISOMER

(71) Applicants: Doron Pappo, Lehavim (IL); Shmuel A. Baron, Ashdod (IL); Sima Mirilashvili, Lod (IL); Yaniv Barda, Rehovot (IL)

(72) Inventors: Doron Pappo, Lehavim (IL); Shmuel A. Baron, Ashdod (IL); Sima Mirilashvili, Lod (IL); Yaniv Barda, Rehovot (IL)

(73) Assignee: ADAMA AGAN LTD., Ashdod (IL)

( * ) Notice: Subject to any disclaimer, the term of this patent is extended or adjusted under 35 U.S.C. 154(b) by 47 days.

(21) Appl. No.: 16/500,271

(22) PCT Filed: Apr. 3, 2018

(86) PCT No.: PCT/IB2018/000446
§ 371 (c)(1),
(2) Date: Oct. 2, 2019

(87) PCT Pub. No.: WO2018/185559
PCT Pub. Date: Oct. 11, 2018

(65) Prior Publication Data
US 2021/0101857 A1 Apr. 8, 2021

Related U.S. Application Data

(60) Provisional application No. 62/481,235, filed on Apr. 4, 2017.

(51) Int. Cl.
*C07C 37/86* (2006.01)
*C07C 39/26* (2006.01)
(52) U.S. Cl.
CPC ............. *C07C 37/86* (2013.01); *C07C 39/26* (2013.01)
(58) Field of Classification Search
CPC .................................. C07C 37/86; C07C 39/26
See application file for complete search history.

(56) References Cited

U.S. PATENT DOCUMENTS

| 4,262,152 A * | 4/1981 | Johnson ................ C07C 201/12 |
| | | 568/775 |
| 4,504,689 A | 3/1985 | Serge |
| 2021/0101857 A1 | 4/2021 | Pappo et al. |

FOREIGN PATENT DOCUMENTS

| CH | 513 586 | 4/1970 | |
| CH | 513 586 A | 10/1971 | |
| CH | 513586 A * | 10/1971 | ............. C07C 37/62 |
| EP | 0 019 388 A1 | 11/1980 | |
| EP | 0 066 217 A1 | 12/1982 | |
| WO | WO 2007/120012 A1 | 10/2007 | |
| WO | WO 2018/185559 A1 | 10/2018 | |

OTHER PUBLICATIONS

International Search Report dated Jul. 12, 2018 in connection with PCT International Application No. PCT/IB2018/000446.
Written Opinion of the International Searching Authority dated Jul. 12, 2018 in connection with PCT International Application No. PCT/IB2018/000446.
First Examination Report dated Mar. 18, 2021 in connection with Indian Application No. 201937032239.
European Communication Rule 161(1) and 162 EPC dated Nov. 12, 2019 in connection with European Patent Application No. EP 18727419.6
Response to European Communication Article 161-162 EPC filed on May 14, 2020 in connection with European Patent Application No. EP18727419.6.
European Communication Article 94(3) EPC dated Apr. 8, 2021 in connection with European Patent Application No. EP 18727419.6.
International Preliminary Report on Patentability dated Oct. 8, 2019 in connection with PCT International Application No. PCT/IB2018/000446.

* cited by examiner

*Primary Examiner* — Rosalynd A Keys
(74) *Attorney, Agent, or Firm* — Gary J. Gershik

(57) ABSTRACT

The present subject matter relates to a process for separating compound (I) from a mixture comprising compound (I). The present subject matter also relates to a process for separating compound (I) from a mixture comprising compound (I) and compound (II).

19 Claims, No Drawings

SEPARATION OF PHENOL ISOMER

CROSS-REFERENCE TO RELATED APPLICATIONS

This application is a § 371 national stage of PCT International Application No. PCT/IB2018/000446, filed Apr. 3, 2018, claiming the benefit of U.S. Provisional Application No. 62/481,235, filed Apr. 4, 2017, the entire content of each of which are hereby incorporated by reference.

This application claims priority of U.S. Provisional Application No. 62/481,235, filed Apr. 4, 2017, the entire content of which is hereby incorporated by reference herein.

Throughout this application various publications are referenced. The disclosures of these documents in their entireties are hereby incorporated by reference into this application in order to more fully describe the state of the art to which this invention pertains.

TECHNICAL FIELD

The present subject matter relates to a process for separating compound (I) from a mixture comprising compound (I). The present subject matter also relates to a process for separating compound (I) from a mixture comprising compound (I) and compound (II).

BACKGROUND

2-Chloro-4-trifluoromethyl-phenol (compound (I)) is used as a reagent in the manufacture of certain nitro diphenyl ether herbicide.

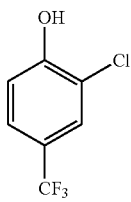

I

Many active ingredients, in different fields such as pharma and agriculture, use compound (I) in their synthetic pathways.

Compound (I) is often used as a starting material.

Compound (I) can be obtained as a by-product and/or residual waste in different manufacturing process such as described in U.S. Pat. No. 4,046,798.

In the residual waste, the compound (I) may exist in a mixture with 2-chloro-5-(trifluoromethyl)-phenol (compound (II)).

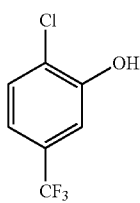

II

The residual waste also may comprise unknown impurities.

In manufacturing processes, impurities can react in parallel synthetic pathways, creating a need for extra further purification steps leading to additional costs. In addition, undesirable side-reactions require an excess of reagents, decrease yields, and increase costs and waste.

Several known procedures such as crystallization, column separation and distillation described in the literature may be used for purifying and isolating specific compound from mixtures or for recycling and converting synthesis mother liquors into reusable material.

For example, U.S. Pat. No. 2,016,848 discloses a method of separating orto and para benzyl phenol isomers via converting the compounds to their salt form and filtrating for one of the isomers. In another example U.S. Pat. No. 4,366,329 discloses a method of separating meta and para bromo phenol isomers via sodium salt derivative.

Separation of compounds depends on the specific structure of the compound to be isolated. The position and location of the functional groups influence the separation method and conditions.

Compounds, such as compound (I), which have multifunctional group wherein at least one of the groups is tri-fluoro methyl are very sensitive and can rapidly undergo hydrolysis, resulting with carboxylic acid. The phenol is sensitive to water in alkali conditions and the Cl moiety can react with a phenol of another molecule.

Each of the separation methods currently known in the art has disadvantages and cannot be used for separating compound (I) from a mixture. Distillation of the mixture causes high corrosion and is accompanied with decomposition of the desirable compound.

Column separation has a very high cost and is a cumbersome procedure. Column separation also requires use of multiple and large amounts of solvents. Conventional isomer separation cannot be used due the multi-functional groups and the type and nature of the functional groups.

There is a need to find an easy, inexpensive procedure to isolate 2-Chloro-4-trifluoromethyl-phenol, i.e. compound (I), from a mixture of isomers and other impurities.

There is also a need to find a method for obtaining 2-Chloro-4-trifluoromethyl-phenol, i.e. compound (I), in high yield, in an easy, low cost, and high selectivity and purity.

SUMMARY

It was found that compound (I) can be isolated and purified without the need for distillation and/or separation by column chromatography.

The present invention provides a process for separating compound (I), or a salt thereof, from a mixture comprising the compound (I),

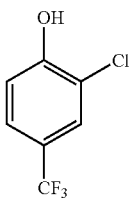

I the process comprising the steps of:
(a) combining the mixture with an amount of a base in the presence of at least one solvent so as to form a precipitate; and
(b) separating the precipitate,
thereby separating the compound (I) from the mixture.

DETAILED DESCRIPTION

Prior to setting forth the present subject matter in detail, it may be helpful to provide definitions of certain terms to be used herein. Unless defined otherwise, all technical and scientific terms used herein have the same meaning as is commonly understood by one of skill in the art to which this subject matter pertains.

The term "a" or "an" as used herein includes the singular and the plural, unless specifically stated otherwise. Therefore, the terms "a," "an," or "at least one" can be used interchangeably in this application.

Throughout the application, descriptions of various embodiments use the term "comprising"; however, it will be understood by one of skill in the art, that in some specific instances, an embodiment can alternatively be described using the language "consisting essentially of" or "consisting of". In each such instance, the terms "comprising," "consisting essentially of," and "consisting of" are intended to have the same meaning as each such term would have when used as the transition phrase of a patent claim.

As used herein, the term "about" specifically includes ±10% from the indicated values in the range. In addition, the endpoints of all ranges directed to the same component or property herein are inclusive of the endpoints, are independently combinable, and include all intermediate points and ranges.

The present invention provides a process for separating compound (I), or a salt thereof, from a mixture comprising the compound (I),

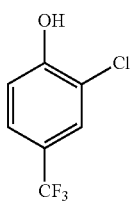

I the process comprising the steps of:
(a) combining the mixture with an amount of a base in the presence of at least one solvent so as to form a precipitate; and
(b) separating the precipitate,
thereby separating the compound (I) from the mixture.
In some embodiments, the mixture further comprises compound (II)

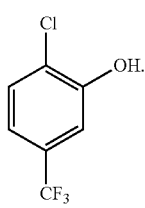

II

The process described herein may be used to separate compound (I) from mixtures with any compound (I) to compound (II) ratio.

In some embodiment, the ratio of compound (I) to compound (II) in the mixture is from 1:1000 to 1000:1.

In some embodiment, the ratio of compound (I) to compound (II) in the mixture is from 90:10 to 70:30. In some embodiments, the ratio of compound (I) to compound (II) in the mixture is 90:10, 85:15, or 80:20, 75:25, or 70:30.

In some embodiments, the ratio of compound (I) to compound (II) in the mixture is 88:11.

In some embodiments, the mixture which comprises compound (I) and compound (II) is a solution.

In some embodiment, the concentration of the compound (I) in the solution is from about 1% to 99%.

In some embodiments, the resulting precipitate material is a metal salt.

In some embodiments, the ratio of compound (I) to compound (II) in the resulting precipitate material is from 50:1 to 1000:1. In some embodiments, the ratio of compound (I) to compound (II) in the resulting precipitate material is from 50:1 to 500:1. In some embodiments, the ratio of compound (I) to compound (II) in the resulting precipitate material is from 50:1 to 200:1. In some embodiments, the ratio of compound (I) to compound (II) in the resulting precipitate material is from 50:1 to 100:1.

In some embodiments, the ratio of compound (I) to compound (II) in the resulting precipitate material is 77:0.4.

In some embodiments, the ratio of compound (I) to compound (II) in the resulting precipitate material is 98.15:1.85.

In some embodiments, the ratio of compound (I) to compound (II) in the resulting precipitate material is 93:0.2.

In some embodiment, the purity of compound (I) in the resulting precipitate material is 80% or more, 85% or more, 90% or more, 95% or more, or 99% or more. In some embodiment, the purity of compound (I) in the resulting precipitate material is 80%, 85%, 90%, 95%, or 99%.

In some embodiment, the purity of compound (I) in the resulting precipitate material is 93%.

In some embodiment, the process further comprises neutralization of the metal salt with an acid. In some embodiment, the metal salt of compound (I) is neutralized with an acid.

In some embodiments, the acid is an organic acid.

Organic acids that may be used include but are not limited to carboxylic acids such as citric acid, fumaric acid, phthalic acid, maleic acid, malic acid, oxalic acid, adipic acid, glutaric acid, 2-methyl glutaric acid, succinic acid and tartaric acid, tri fluoro methyl acetic acid, p-toluene sulfonic acid or any combination thereof.

In some embodiments, the acid is an inorganic acid.

Inorganic acids that may be used include but are not limited to hydrochloric acid, hydrobromic acid, hydroiodic acid, nitric acid, sulfuric acid, persulfuric acid or any combination thereof.

In some embodiments, the mixture reacts with the base in the presence of at least two solvents.

In some embodiments, the mixture reacts with the base in the presence of at least three solvents.

In some embodiments, the mixture reacts with the base in the presence of at least four solvents.

In some embodiments, at least one of the solvents is a polar solvent. In some embodiments, the polar solvent is an organic polar solvent.

In some embodiments, the organic polar solvent is dimethyl sulfoxide (DMSO), dimethylformamide (DMF), N-Methyl-2-pyrrolidone (NMP), glycols, sulfolan, mono and di-glymes, acetamide, glycerine, ACN, nitro ethane or any combination thereof.

In some embodiments, the organic polar solvent is an alcohol. In some embodiments, the alcohol is methanol, ethanol or propanol. In preferred embodiments, the alcohol is ethanol.

In some embodiments, at least 1% of the total volume of the solvent is polar solvent.

In some embodiments, at least one of the solvents is a nonpolar solvent. In some embodiments, the nonpolar solvent is an organic nonpolar solvent.

In some embodiments, the nonpolar solvent is nonpolar aromatic solvent. In some embodiments, the nonpolar aromatic solvent is toluene, xylene, mono chloro benzene (MCB), naphtha, or any combination thereof. In preferred embodiments, the nonpolar aromatic solvent is toluene.

In some embodiments, the naphtha is light naphtha. In some embodiments, the naphtha is heavy naphtha. In some embodiments, the naphtha is petroleum naphtha. In some embodiments, the solvent naphtha is the Solvesso® grades from ExxonMobil Chemical, especially Solvesso® 100 (CAS No. 64742-95-6), Solvesso® 150 (CAS No. 64742-94-5), and Solvesso® 200 (CAS No. 64742-94-5).

In some embodiments, the nonpolar aromatic solvent has a flashpoint of about 100° F. to about 200° F. In some embodiments, the nonpolar aromatic solvent has a flashpoint of about 100° F. In some embodiments, the nonpolar aromatic solvent has a flashpoint of about 150° F. In some embodiments, the nonpolar aromatic solvent has a flashpoint of about 200° F.

In some embodiments, none of the solvents is a nonpolar aromatic solvent.

In some embodiment, the nonpolar solvent is pentane, hexane, or dichloromethane (DCM).

In some embodiments, one of the solvents is water. In some embodiments, the water is added to the reaction mixture. In some embodiments, the water is formed during the reaction. In some embodiments, the water is formed with addition of the base into the reaction mixture.

In some embodiments, at least 1% of the total volume of the solvent is water.

In some embodiments, the mixture is solution. In some embodiments, the mixture is solid.

In some embodiments, the concentration of water in the aqueous solution is not more than 25%. In some embodiments, the concentration of water in the aqueous solution is 10%. In some embodiments, the concentration of water in the aqueous solution is 1%.

In some embodiments, the mixture reacts with the base in the presence of one solvent wherein the solvent is ethanol. In some embodiments, the mixture reacts with the base in the presence of at least one solvent wherein one of the solvent is ethanol.

In some embodiments, the mixture reacts with the base in the presence of two solvents wherein the two solvents are toluene and ethanol. In some embodiments, the mixture reacts with the base in the presence of at least two solvents and two of the solvents are toluene and ethanol.

In some embodiments, the mixture reacts with the base in the presence of three solvents wherein the three solvents are toluene, water, and ethanol. In some embodiments, the mixture reacts with the base in the presence of at least three solvents and three of the at least three solvents are toluene, water, and ethanol.

In some embodiments, the base is an organic base. In some embodiments, the base is an inorganic base.

In some embodiments, the base is an alkali metal base. In some embodiments, the base is an earth alkaline metal base. In some embodiments, the alkaline metal is sodium, lithium, or potassium. In some embodiments, the earth alkaline metal is magnesium or calcium.

In some embodiments, the organic base is triethylamine, trimethylamine, ammonia, ammonium hydroxide, pyridine, guanidines, tetramethylammonium hydroxide, tetrabutylammonium hydroxide, choline hydroxide, or 1,4-diazabicyclo[2.2.2]octane (DABCO).

In some embodiments, the inorganic base is hydroxy, alkoxy, carbonate, or bicarbonate.

In some embodiments, the carbonate base is lithium carbonate, sodium carbonate, sodium bicarbonate, potassium carbonate, potassium bicarbonate or any combination thereof.

In preferred embodiments, the base is potassium hydroxide. In preferred embodiments, the base is sodium hydroxide.

In some embodiments, the base is dissolved in the solvent. In some embodiments, the base is dissolved in water. In some embodiments, the base contains water. In some embodiments, the base is dissolved in an organic solvent.

In some embodiments, the process is performed at a temperature below 50° C. In some embodiments, the temperature is 20° C. to 40° C. In some embodiments, the temperature is 15-22° C. In some embodiments, the temperature is 45° C., 40° C., 35° C., 30° C., 25° C., 20° C., 15° C., 10° C. In specific embodiment, the temperature is 30° C.

In some embodiments, the resulting precipitate material is a solid. In some embodiments, the resulting precipitate material is a paste.

In some embodiments, the resulting precipitate material is separated in step (b) by filtration. In some embodiments, the resulting precipitate material is separated in step (b) by centrifuge. In some embodiments, the resulting precipitate material is separated in step (b) by decantation.

The subject invention also provides a method of obtaining the compound of formula (I)

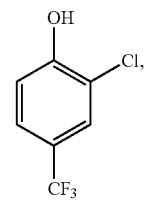

I comprising separating the compound of formula (I) according to any embodiments of the present invention.

The subject invention also provides a compound (I)

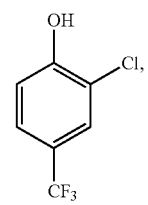

I or a salt thereof,
separated using the process described herein.

The subject invention also provides a compound (I)

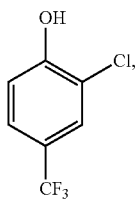

or a salt thereof.

In some embodiments, the salt of the compound (I) is a metal salt.

In some embodiments, the metal salt is a potassium salt.

The subject invention also provides a composition comprising a compound (I), or a salt thereof.

In some embodiments, the salt of the compound (I) is a metal salt.

In some embodiments, the metal salt is a potassium salt.

In some embodiments, the composition further comprises a base.

In some embodiments, the base is potassium hydroxide.

The subject invention also provides a composition comprising a precipitate and at least one solvent, wherein the precipitate comprises a salt of compound (I)

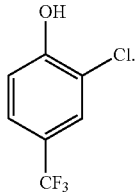

In some embodiments, the salt of the compound (I) is a metal salt.

In some embodiments, the metal salt is a potassium salt.

In some embodiments, the composition comprises at least two solvents. In some embodiments, the composition comprises at least three solvents. In some embodiments, the composition comprises at least four solvents.

In some embodiments, at least one of the solvents is a polar solvent. In some embodiments, the polar solvent is an organic polar solvent.

In some embodiments, the organic polar solvent is dimethyl sulfoxide (DMSO), dimethylformamide (DMF), N-Methyl-2-pyrrolidone (NMP), glycols, sulfolan, mono and di-glymes, acetamide, glycerine, ACN, nitro ethane or any combination thereof.

In some embodiments, the organic polar solvent is alcohol. In some embodiments, the alcohol is methanol, ethanol or propanol. In preferred embodiments, the alcohol is ethanol.

In some embodiments, at least 1% of the total volume of the solvent is polar solvent.

In some embodiments, at least one of the solvents is a nonpolar solvent. In some embodiments, the nonpolar solvent is an organic nonpolar solvent.

In some embodiments, the nonpolar solvent is nonpolar aromatic solvent. In some embodiments, the nonpolar aromatic solvent is toluene, xylene, mono chloro benzene (MCB), naphtha, or any combination thereof. In preferred embodiment, the nonpolar aromatic solvent is toluene.

In some embodiments, the naphtha is light naphtha. In some embodiments, the naphtha heavy naphtha. In some embodiments, the naphtha is petroleum naphtha. In some embodiments, the solvent naphtha is the Solvesso® grades from ExxonMobil Chemical, especially Solvesso® 100 (CAS No. 64742-95-6), Solvesso® 150 (CAS No. 64742-94-5), and Solvesso® 200 (CAS No. 64742-94-5).

In some embodiments, none of the solvents is a nonpolar aromatic solvent.

In some embodiment, the nonpolar solvent is pentane, hexane, or dichloromethane (DCM).

In some embodiments, one of the solvents is water.

In some embodiments, the composition comprises one solvent wherein the solvent is ethanol.

In some embodiments, the composition comprises two solvents wherein the two solvents are toluene and ethanol.

In some embodiments, the composition comprises three solvents wherein the three solvents are toluene, water, and ethanol.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

The invention is illustrated by the following examples without limiting it thereby.

EXPERIMENTAL SECTION

Example 1

Procedure for Isolation of
2-chloro-4-trifluoromethyl phenolate

Into a three neck round bottom flask equipped with a mechanical stirrer, dropping funnel and thermometer were added toluene (350 g), ethanol (25 g), water (15 g) and potassium hydroxide flakes (90 g). The mixture was stirred at room temperature for 1 hour. A mixture (300 g, 1.53 mol of phenols mixture) of 2-chloro-4-(trifluoromethyl)-phenol, i.e. compound (I), and 2-chloro-5-(trifluoromethyl)-phenol, i.e. compound (II), was added dropwise, during 45 minutes, at such a rate that the temperature maintained at 15-22° C. The mixture was stirred at room temperature for 3 hours until all the KOH has disappeared (the color of the mixture was brown), and a brown solid was formed. The solid was filtered, washed with toluene (50 g) and dried at 30° C. under reduced pressure to afford phenoxy-K (hydrate)(306 g). The filtered solid comprised compound (I) and compound (II) in of ratio of 93:0.2.

Example 2

Procedure for Isolation of
2-chloro-4-trifluoromethyl phenolate

Mother liquor from U.S. Pat. No. 4,046,798 Example 3 or Chinese Patent Application No. CN1363548A Example 5 (600 g) were evaporated under reduced pressure at room temperature to obtain about 300 g residue, which contains a mixture of 2-chloro-4-(trifluoromethyl)-phenol, i.e. compound (I), 2-chloro-5-(trifluoromethyl)-phenol, i.e. compound (II), and other impurities.

Into a three neck round bottom flask equipped with a mechanical stirrer, dropping funnel and thermometer were added toluene (350 g), ethanol (25 g), water (15 g) and potassium hydroxide flakes (90 g). The mixture was stirred at room temperature for 1 hour and then the above residue left from the mother liquor evaporation (300 g) was added dropwise, during 45 minutes, at such a rate that the temperature maintained at 15-22° C. The mixture was stirred at room temperature for 3 hours until all the KOH has disappeared (the color of the mixture was brown), and a brown solid was formed. The solid was filtered, washed with toluene (50 g) and dried at 30° C. under reduced pressure to afford phenoxy-K (hydrate) (306 g) (ratio of compound (I) to compound (II) was 93:0.2).

Example 3

Procedure for Isolation of
2-chloro-4-trifluoromethyl phenolate (in Ethanol)

Into a three neck round bottom flask equipped with a mechanical stirrer, dropping funnel and thermometer were added ethanol (150 g) and potassium hydroxide flakes (32 g). The mixture was stirred at room temperature for 1 hour and then a mixture (100 g) of 2-chloro-4-(trifluoromethyl)-phenol, i.e. compound (I) and 2-chloro-5-(trifluoromethyl)-phenol, i.e. compound (II), were added dropwise, during 45 minutes, at such a rate that the temperature maintained at 15-20° C. The ratio of compound (I) to compound (II) in the mixture was 95:5. The mixture was stirred at room temperature for 18 hours. No solid was formed. Ethanol was distilled out until a precipitation was observed. The solid was filtered and dried at 30° C. under reduced pressure to afford phenoxy-K (hydrate) (18.8 g) (ratio of compound (I) to compound (II) was 98.15:1.85).

REFERENCES

1. U.S. Pat. No. 2,016,848, issued Oct. 8, 1935 (Akimoff et al.).
2. U.S. Pat. No. 4,366,329, issued Dec. 28, 1982 (Raynolds et al.).

What is claimed is:

1. A process for separating compound (I), or a salt thereof, from a mixture comprising the compound (I),

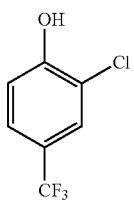

I the process comprising the steps of:
(a) combining the mixture with an amount of a base in the presence of at least one solvent so as to form a precipitate; and
(b) separating the precipitate,
thereby separating the compound (I) from the mixture, wherein the mixture further comprises compound (II)

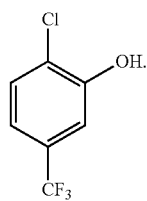

II

2. The process of claim 1, wherein:
a) the ratio of compound (I) to compound (II) in the mixture is from 1:1000 to 1000:1,
b) the ratio of compound (I) to compound (II) in the mixture is from 90:10 to 70:30, or
c) the ratio of compound (I) to compound (II) in the mixture is 88:11.

3. The process of claim 1, wherein:
a) the base is an organic base or an inorganic base, and/or
b) the base contains water.

4. The process of claim 3, wherein:
a. the organic base is triethylamine, trimethylamine, ammonia, ammonium hydroxide, pyridine, guanidines, tetramethylammonium hydroxide, tetrabutylammonium hydroxide, choline hydroxide, or 1,4-diazabicyclo[2.2.2]octane (DABCO), or
b. the inorganic base is an alkali metal base, earth alkaline metal base, hydroxy base, alkoxy base or carbonate base.

5. The process of claim 4, wherein:
a. the alkali metal base is a sodium base, lithium base, or potassium base,
b. the earth alkaline metal base is a magnesium base or calcium base, or
c. the carbonate base is lithium carbonate, sodium carbonate, sodium bicarbonate, potassium carbonate or potassium bicarbonate.

6. The process of claim 1, wherein the mixture reacts with the base in the presence of at least two solvents.

7. The process of claim 1, wherein:
a) at least one of the solvents is a polar solvent selected from alcohol, dimethyl sulfoxide (DMSO), dimethylformamide (DMF), N-Methyl-2-pyrrolidone (NMP), glycols, sulfolan, mono and di-glymes, acetamide, glycerine, acetonitrile (ACN), nitro ethane, and any combination thereof, and/or
b) at least one of the solvents is a nonpolar solvent selected from toluene, xylene, mono chloro benzene (MCB), naphtha, pentane, hexane, or dichloromethane (DCM) and any combination thereof.

8. The process of claim 7, wherein the alcohol is methanol, ethanol or propanol.

9. The process of claim 1, wherein the mixture is an aqueous solution and the concentration of water in the aqueous solution is not more than 25%.

10. The process of claim 1, wherein:
a. the mixture reacts with the base in the presence of one solvent and the solvent is ethanol,
b. the mixture reacts with the base in the presence of two solvents and the solvents are toluene and ethanol, or
c. wherein the mixture reacts with the base in the presence of three solvents and the solvents are toluene, ethanol and water.

11. The process of claim 1, wherein:
a) step a) of the process is performed at a temperature below 50° C.,
b) the precipitate is separated in step (b) by filtration, by centrifuge, or by decantation, and/or
c) the precipitate comprises a metal salt of the compound (I).

12. The process of claim 11, wherein:
a. the precipitate further comprises a metal salt of the compound (II) wherein the ratio of the metal salt of compound (I) to the metal salt of compound (II) in the precipitate is from 50:1 to 1000:1, and/or
b. the purity of the salt of compound (I) in the precipitate is 80% or more, 85% or more, 90% or more, 95% or more, or 99% or more.

13. The process of claim 11, wherein the process further comprises neutralizing the metal salt of compound (I) with an acid.

14. The process of claim 13, wherein the acid is carboxylic acids, fumaric acid, phthalic acid, maleic acid, malic acid, oxalic acid, adipic acid, glutaric acid, 2-methyl glutaric acid, succinic acid, tartaric acid, tri fluoro methyl acetic acid, p-toluene sulfonic acid, hydrochloric acid, hydrobromidic acid, hydroiodic acid, nitric acid, sulfuric acid, persulfuric acid or any combination thereof.

15. A method of obtaining a compound (I)

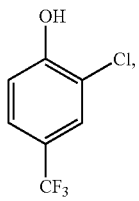

comprising separating the compound (I) according to the process of claim 1.

16. The process of claim 1, wherein the base is potassium hydroxide.

17. The process of claim 1, wherein the solvent is ethanol.

18. The process of claim 1, wherein the mixture reacts with the base in the presence of at least two solvents or at least three solvents.

19. The process of claim 18, wherein:
   a. the mixture reacts with the base in the presence of two solvents and the two solvents are toluene and ethanol, or
   b. the mixture reacts with the base in the presence of three solvents and the three solvents are toluene, ethanol and water.

* * * * *